United States Patent [19]

Rosenberg et al.

[11] 4,135,524
[45] Jan. 23, 1979

[54] PROCESS FOR REDUCING CRITICAL SURFACE TENSION AND COEFFICIENT OF FRICTION IN HAIR

[75] Inventors: Ira E. Rosenberg, West Norwalk; John A. Ferguson, Darien; Norman P. Loveless, Fairfield, all of Conn.

[73] Assignee: Clairol Incorporated, New York, N.Y.

[21] Appl. No.: 782,679

[22] Filed: Mar. 30, 1977

[51] Int. Cl.$^2$ .................. A45D 7/00; A61K 7/00; A61K 7/06; A61K 7/09
[52] U.S. Cl. ................................ 132/7; 424/47; 424/70; 424/71
[58] Field of Search ................ 424/70, 71, 47; 132/7

[56] References Cited
U.S. PATENT DOCUMENTS 3,972,998  8/1976  Keiner .................................. 424/70

Primary Examiner—Donald B. Moyer
Attorney, Agent, or Firm—Irving Holtzman; George A. Mentis; David J. Mugford

[57] ABSTRACT

A process for treating hair to reduce its critical surface tension and/or coefficient of friction by applying to said hair a composition comprising a fluoropolymer containing as monomers at least:

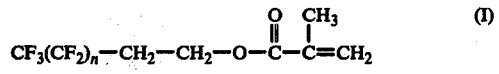

wherein n is a number of about 7 to 11 inclusive; and

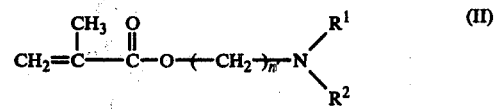

in which n' is a number of about 2 to 4 inclusive and $R^1$ and $R^2$ are lower alkyl, preferably having 1-4 carbon atoms or its N-oxides or salts. In a preferred form the fluoropolymer also contains:

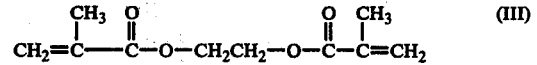

18 Claims, No Drawings

PROCESS FOR REDUCING CRITICAL SURFACE TENSION AND COEFFICIENT OF FRICTION IN HAIR

This invention relates to a process for treating human hair and especially to a process for treating human hair on the head and to compositions that are useful for this process. More particularly, it concerns a process for treating hair for the purpose of reducing its critical surface tension and its coefficient of friction. The reduction in critical surface tension is important in that this serves to reduce the drying time of hair treated according to this invention that has been rewetted. This is also important in that hair having this resulting characteristic remains cleaner longer; retarding the build up of natural oils and dirt. The reduction in coefficient of friction is significant in that hair exhibiting this characteristic has a greater ease of combing in the dry state.

The process of the present invention also gives hair greater stylability and manageability. Hair which has been treated in accordance with this process upon rewetting has improved manageability and stylability. In addition, the compounds by themselves or when used in conjunction with antistatic agents, reduce the "flyaway" of hair.

It has been found that the aforesaid beneficial properties may be imparted to hair by treating said hair with a vehicle containing one or more of a certain class of fluoropolymers. These fluoropolymers can be defined as polymers formed by the polymerization of at least two monomers i.e. a fluoroalkylmethacrylate and an aminoalkylmethacrylate. The latter can be employed as such or can be utilized in the form of an N-oxide or as a salt including the quaternary amine salts. In some instances, it is also useful to add a third monomer to the polymer that can be described generally as an alkylenedimethacrylate.

More particularly, the fluoropolymers that are useful herein are formed from at least a monomer defined by the formula:

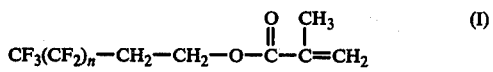

wherein n is a number of about 7 to 11 inclusive; hereinafter called Monomer I and a monomer of formula:

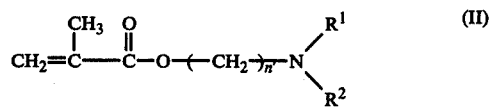

its N-oxides or its salts including its quaternary ammonium salts wherein n' is a number of about 2 to 4 inclusive and $R^1$ and $R^2$ are lower alkyl, preferably having 1-4 carbon atoms; hereinafter called Monomer II.

When an alkylenedimethacrylate monomer is also employed in forming the fluoropolymers that are used herein it is preferably one of formula:

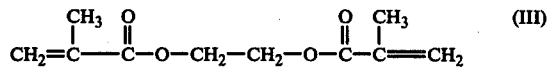

hereinafter referred to as Monomer EDM.

The aforesaid monomers can be used in varying proportions in formulating the polymer that can be employed in the present invention. Ordinarily, however, the monomer will be present within the following ranges:

|  | % wt. based on wt. of polymer |
| --- | --- |
| Monomer I | 60 to 90 |
| Monomer II or its N-oxide or salt | 5 to 25 |
| Monomer EDM | 0 to 10 | the sum of the percentages of monomers present in the fluoropolymer being 100%. When Monomer EDM appears in the polymer, it will usually comprise about from 0.01% to 10% by weight of the polymer. In the preferred case, the ratio of monomers I/II/EDM is 84.98/15/0.02.

As noted, Monomer II may be used in the form of a salt, including quaternary amine salts. Typical among the salts that may be employed are the acetate, the propionate, the hydrochloride, the hydrobromide, etc. As examples of the quaternary amine salts that can be employed, mention may be made of those formed from dimethyl sulfate, diethyl sulfate, methyl chloride, etc.

These polymers may be prepared using processes that are well known to those skilled in this art. Typical suitable procedures are described in U.S. Pat. No. 3,462,296. The preferred method of preparing these fluorinated polymers is by solution polymerization. Emulsion polymerization may also be employed. For example, one can pre-emulsify the water insoluble monomers, using dimethyloctadecylamine acetate as the dispersing agent, and then combine this emulsion with a water solution of the water soluble monomers. Azo bis(isobutyramidine)dihydrochloride or a large variety of peroxides such as benzoyl peroxide or di-tertbutyl peroxide can be used to initiate the reaction. The inherent viscosities of the polymers used in this invention are measures of the degree of polymerization. In general, these will be of the order shown in Column 3, line 12 through 20 of U.S. Pat. No. 3,462,296.

The compositions that are useful in practicing the process of the present invention may vary somewhat with respect to the quantity of the fluoropolymer contained therein. This might vary according to the results desired, the vehicle employed, etc. In general, however, the fluoropolymer will comprise about 0.005% to 30% by weight based on the total weight of the composition and preferably from about 0.1% to 5% by weight.

The vehicle or carrier for the fluoropolymer that can be employed in accordance with the present invention may take a variety of forms. The fluoropolymer may be incorporated in a solvent system or some other liquid system in the form of a true solution, a dispersion, an emulsion or a lotion. Moreover, the fluoropolymer may be incorporated in a cream, gel or foam base or incorporated in an aerosol propellant system. These compositions may also include other adjuvants or assistants that are useful in preparing cosmetically elegant products or imparting other useful properties to the hair. By way of illustrating the other adjuvants that may also be incorporated in the present composition, the following is given: coupling agents, plasticizers, emollients, thickeners, lubricants, resins, penetrants, buffering agents, surfactants, dyes and other colorants, preservatives, medicaments, UV absorbers, perfumes, protein hydrolzates and other protein derivatives, brilliance modifiers, conditioners, antistatic agents, anti-hygroscopic agents, clarifiers, evaporation accelerators, foaming or defoaming agents, and the like. These when present will generally be present in relatively low proportion e.g. from about 0.01 to 5% by weight based on the weight of the composition.

When the composition takes the form of an aerosol product, any of the known aerosol propellants may be used in formulating the product. For example, the propellant may be gaseous such as carbon dioxide, nitrous oxide or nitrogen or mixtures thereof, or one of a mixture of liquified normally gaseous propellants including hydrocarbons such as propane, n-butane and isobutane and low boiling halohydrocarbons such as methylene chloride, 1,1,1-trichloroethane, and the fluorinated hydrocarbons generally available variously under the designations "Freon" (E. I. DuPont), "Genetron" (Allied Chemical), and "Isotron" (Pennwalt Chemical). Illustrative of the latter types are trichloromonofluoromethane, dichlorodifluoromethane; dichlorotetrafluoroethane, 1-chloro-1,1-difluoroethane, 1,1-difluoroethane, monobromomonochlorodifluoromethane and the like. Mixtures of gaseous and liquified normally gaseous propellants may also be employed such as trichlorofluoromethane and about 2 to 10% by weight of nitrous oxide.

When the product takes the form of an aerosol product, the actives i.e. the fluoropolymer or the mixture of fluoropolymers may be added as such to the propellant or may be added as a concentrate in a liquid or solvent system. In this case, the propellant will comprise between about 20% to 90% by weight based on the total weight of the composition; the balance being made up by the actives or the concentrate containing the actives.

In the preferred form of the invention, the vehicle employed is an aqueous system in which the fluoropolymer is soluble. The solvent system may comprise the single solvent, water, or a combination of water and organic solvents; preferably those organic solvents which are volatile. Typical organic solvents that may be employed for these purposes included the lower alkanols e.g. containing 2 to 4 carbons e.g. ethanol, n-propanol, isopropanol; hydroalcoholic solvents (e.g. ethanol-water); ester solvents such as ethyl acetate, amyl acetate; halogenated hydrocarbons (e.g. methylene chloride, Freon 11, Freon 114).

The general procedure for practicing the process of the present invention is to apply the fluoropolymer containing composition to the hair in sufficient quantities so that the hair is thoroughly coated with the polymer. Depending upon the ultimate effect to be obtained and the other components of the composition, the hair so treated may be either rinsed or left unrinsed. The fluoropolymers of the present compositions are sufficiently substantive to the hair that a significant amount remains on the hair after it is rinsed. If used as a "leave in product", the composition may be applied as a spray after which the hair may be towel dried or dried in any other suitable fashion and then, if desired, styled. If used as a "rinse-out product" the composition may be applied in the shower after shampooing. The product is left on the hair for a reasonable period of time (e.g. ½ to 30 minutes) after which it is rinsed out with warm water. The hair is then dried and styled in the usual manner.

As noted above, in the application of products of this invention, it is advantageous to dry the hair. Any of the usual methods may be used for this purpose. However, optimum results and efficiency are obtained when the hair is blown dry as, for example, by using hot air hair blow dryers.

PRIOR ART

It is known in the prior art that applying fluorine containing polymers to hair imparts water repellency thereto and reduces sebum buildup. They are also known to improve the holding characteristics of other resins that are also applied to the hair. However, there is no suggestion therein for the use of the polymers employed in the present invention.

Canadian Pat. No. 940,049 teaches that copolymers of fluorine containing monomers can be used to impart water repellency to hair. The vinyl monomers used in the patent have the general formula:

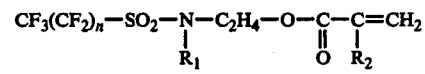

wherein $R_1$ is an alkyl group containing 1 to 6 carbon atoms, $R_2$ is hydrogen or methyl and n is an integer from 3 to 11. The major claim made in it is that these fluoropolymers when incorporated into a shampoo, a waving composition, a setting composition, a bleaching composition, a colorant composition or a conditioning composition, help reduce the drying time of hair. The use of the fluoropolymers employed in the present invention is not disclosed.

U.S. Pat. No. 3,959,462 teaches that 3,3,4,4-tetrafluoro-4-heptafluoroisopropyl butylmethacrylate when homopolymerized or copolymerized with non-fluorinated vinyl monomers and incorporated in hair cleaning products will reduce the rate of sebum flow and thus, prevent sebum buildup on hair. These are not the fluoropolymers used herein.

U.S. Published Patent application No. B-464,491 teaches that fluoroethyl alcohols attached to the backbone of methyl vinyl ether-maleic anhydride copolymers (e.g. Gantrez AN 119) will impart excellent holding characteristics at high relative humidity and impart a soft hand and natural sheen to hair. This too does not disclose the use of the fluoropolymers employed in the present invention.

U.S. Pat. No. 3,972,998 discloses a method for reducing the drying time of hair by applying thereto a composition containing certain vinyl polymers of a fluorine containing monomer having the general structure:

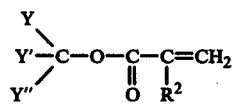

This, also, is far removed from the fluoropolymers employed in this invention.

The following terms used in the specification and Examples given below are defined as set forth below:

| Trade Name | CTFA Adopted Name and/or Structure |
|---|---|
| Lantrol AWS | PEG-75 Lanolin Oil - is the ethoxylated polymer of lanolin oil in which the average degree of ethoxylation is 75 moles of ethylene oxide |
| Brij 30 | Laureth-4 - is an ethoxylated |

-continued

| Trade Name | CTFA Adopted Name and/or Structure |
|---|---|
| | ether of lauryl alcohol $CH_3(CH_2)_{10}CH_2(OCH_2CH_2)_nOH$  n=4 |
| Pluronic P-104 | Poloxamer 334 is a polyoxyethylene polyoxypropylene block polymer that conforms to the general formula $$HO(CH_2CH_2O)_x \left( \begin{array}{c} CH-CH_2O \\ | \\ CH_3 \end{array} \right)_y (CH_2CH_2O)_zH$$ where the percent poly(oxyethylene) (x and z) averages 30% in the total molecule, and the typical weight of the y poly(oxypropylene) averages 3250 |
| Klucel | Hydroxypropyl cellulose |
| Polyquat H | A resin polymer made by Henkel. Based on polyglycol-polyamine condensation |
| Amphoterge S | 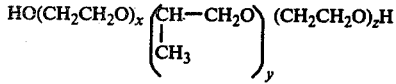 |

Monomer FAM: A commercial product consisting of a mixture of monomers of formula:

$$CF_3(CF_2)_n-CH_2-CH_2-O-\overset{O}{\underset{\|}{C}}-\overset{CH_3}{\underset{|}{C}}=CH_2$$

in which n is 7, 9 or 11 respectively.
Monomer DAEM:

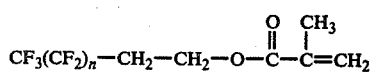

Monomer EDM:

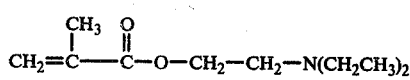

The following are the definitions, the identification, and description of various fluoropolymers used in this invention; they are all used as 15% solutions in isopropanol/water solvent 25/75.

| Fluoropolymer | % by wt. of Monomer | | |
|---|---|---|---|
| | FAM | DAEM | EDM |
| F-55 | 85 | 15 acetate | — |
| F-56 | 84.95 | 15 acetate | .05 |
| F-57 | 83.5 | 15 acetate | 1.5 |
| F-58 | 84.5 | 15 acetate | 0.5 |
| F-59 | 84.98 | 15 acetate | .02 |
| F-60 | 84.0 | 15 acetate | 1.0 |
| F-61 | 84.95 | 15 | .05 |

| Fluoropolymer | % by wt. of Monomer | | |
|---|---|---|---|
| | FAM | DAEM | EDM |
| F-62 | 83.5 | N-oxide 15 | 1.5 |
| F-63 | 84.7 | N-oxide 15 | 0.3 |
| F-64 | 84.98 | N-oxide 15 | .02 |
| F-65 | 85 | N-oxide 15 | — |
| F-66 | 75 | N-oxide 28 | — |
| F-67 | 70 | dimethyl sulfate quat. 30 dimethyl sulfate quat. | — |

In the Examples given below the quantities of fluoropolymers are given as percent by weight of actives, that is as percent by weight of the polymer contained in the total composition and not the percent of the solution of polymer as it is supplied.

The following Examples are given to further illustrate this invention. It is to be understood, however, that this invention is not limited thereto.

EXAMPLE 1

| | % by weight |
|---|---|
| Fluoropolymer F-64 | 0.175 |
| Amphoterge S | 0.0175 |
| Ethanol | 10.00 |
| Water | q.s. |

The Fluoropolymer F-64 and Amphoterge S were added, with stirring to the water. The ethanol was added and the solution was stirred for five minutes.

In the preferred form of the invention, the solution of Example 1 is applied to towel dried hair by spraying the composition onto the hair with a mechanical pump. The hair is subsequently blow dried and styled with an electromechanical hair dryer. Mechanical action tends to spread the fluoropolymer uniformally over the hair fibers to produce the maximum effects.

Examples 2 through 12 are listed in tabular form. The solutions were prepared by dissolving or dispersing the ingredients in water. Ethanol was then added. In the case of Example 9, the fragrance was added to the ethanol and then mixed with the water phase.

In Examples 2 through 10 the product was applied to the hair with a mechanical sprayer and the hair was dried and styled in the normal manner. In Examples 11 and 12 the product was poured onto the hair after shampooing, rubbed into the hair with the hands, and rinsed off with water. The hair was then dried and styled in the usual manner.

The solutions of Examples 2 through 12 can be applied to wet hair, towel dried hair or dry hair by spraying, rubbing, pouring or combing the compositions into the hair. The hair so treated can be subsequently dried and/or styled by electromechanical means such as electric hair dryers, electric combs or electrically heated rollers, or by natural means such as air drying.

| | % by Weight | | | | | | | | | | |
|---|---|---|---|---|---|---|---|---|---|---|---|
| | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
| Fluoropolymer F-64 | .18 | .18 | .18 | .18 | .18 | .18 | .18 | .20 | .50 | .18 | .18 |
| Amphoterge A | .50 | — | — | — | — | — | — | .02 | — | .02 | .02 |
| Lantrol AWS | — | .50 | — | — | — | — | — | .50 | — | — | — |
| Brij 30 | — | — | .50 | — | — | — | — | — | — | — | — |
| Pluronic P-104 | — | — | — | 1.0 | — | — | — | .75 | — | 1.0 | 1.0 |
| Polyquat H | — | — | — | — | .18 | — | — | — | — | — | — |
| Sodium Citricate | — | — | — | — | — | 1.0 | — | — | — | — | — |
| Sodium Bicarbonate | — | — | — | — | — | — | 1.0 | — | — | — | — |
| Klucel | — | — | — | — | — | — | — | — | — | 1.5 | .75 |
| Fragance | — | — | — | — | — | — | — | .25 | .25 | — | — |
| Ethanol (SDA-40) | 10.0 | 20.0 | 20.0 | 20.0 | 20.0 | 20.0 | 20.0 | 15.0 | 20.0 | 20.0 | 20.0 |
| Water | q.s | q.s | q.s. | q.s. | q.s. | q.s. | q.s. | q.s. | q.s. | q.s. | q.s. |

It has been determined that the fluoropolymer containing compositions described above when used to treat hair in accordance with the present invention increase the water and oil repellency of hair. The increase in water repellency has been demonstrated by critical surface tension and rate of drying measurements of hair that has been treated. The oil repellency has been shown using the method described in U.S. Pat. No. 3,959,462 for measurement of retardation of the flow of sebum.

Since water repellency is a surface phenomenon, an understanding of this requires a study of the effect that treatment of hair has on the surface of hair shaft. A convenient way to quantify surface changes is through the contact angle and critical surface tension.

Contact angle ($\theta$) of a liquid is defined as the angle between the horizontal surface and a line tangent to the surface of the droplet of said liquid at the point of contact of the surface. This is illustrated below:

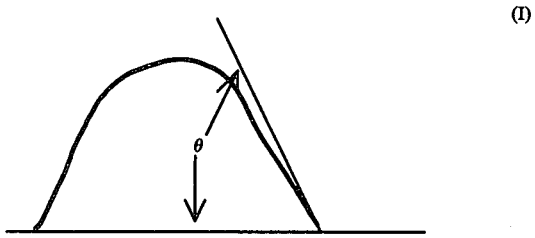

(I)

The relationship between contact angle and surface energy is inverse. That is, a high energy surface is one which allows a liquid to spread out or "wet" the surface so as to decrease its contact angle. A low energy surface prohibits the liquid from spreading, and thus, $\theta$ is larger (> 90°).

If contact angles are determined on a specific solid with liquids of varying surface tensions ($\gamma$) a value for critical surface tension ($\gamma_c$) may be obtained. The method involves extrapolation of the $\gamma$ vs cos $\theta$ line to cos $\theta$ = 1 (zero contact angle). This is the point where the liquid will totally wet the solid.

Mutchler, Menkart and Schwartz (J. P. Mutchler, J. Menkart, and A. M. Schwartz, Pesticidal Formulations Research, Advances in Chemistry Series 86, 7 1967) devised the "Sink-Float" method for determining critical surface tensions of fibers which eliminated the errors associated with measuring contact angles. Small snippets of the fiber were placed on liquids of decreasing surface tension. The critical surface tension lies between the $\gamma$ of the liquid on which the fiber floats, and the $\gamma$ of the liquid in which the fibers sinks.

The principle behind this method is as follows: The hair fiber has a density of ~ 1.35 g/cm$^3$. The liquids used in the test all have densities less than 1.35 g/cm$^3$. The hair fiber would thus sink in the liquid if it were not for buoyant forces of the liquid. These buoyant forces are the surface tension of the liquid. If the surface tension is lowered enough, the liquid cannot overcome the density difference, and the hair fiber sinks. The reported value for the CST (i.e. critical surface tension) of the human hair is between 27.0 (sink) and 27.8 dyne/cm (float).

Using the procedure of Mutchler et al described above, the critical surface tension was determined for hair treated with compositions containing a fluoropolymer according to the present invention. Hair swatches were washed in a 1.00% anionic detergent solution for 5 minutes, rinsed for 5 minutes, and placed at 46° C. for 2 hours until dry. The swatches were then immersed for 5 minutes, in a solution of fluoropolymer made as follows:

| Fluoropolymer F-64 | 0.175% |
|---|---|
| Water | 99.825% |

The swatches were placed in a drying chamber at 46° C. for 6 hours. Small snippets of hair 1 cm. long were cut from the center portion of the hair swatch. Critical surface tension measurements were then made on these hair snippets.

It was found that the critical surface tension of the hair so treated was reduced to less than 15.9 dynes/cm. This composition is so effective in reducing the critical surface tension that a liquid has not yet been found in the present investigation which will sink the hair fiber without removing the terfluoropolymer coating.

It is also of interest to note that general correlation exists between $\gamma_c$ and drying time. Hair samples with $\gamma_c$ of 18.3 dynes/cm or less also show significant decrease in water pickup.

The water repellency effect imparted to hair by the process of this invention may be demonstrated by water uptake and drying time measurements. To better understand this, it will be useful to define some of the terms used in the measurement of water repellency. These terms require basic familiarity with the concept of drying.

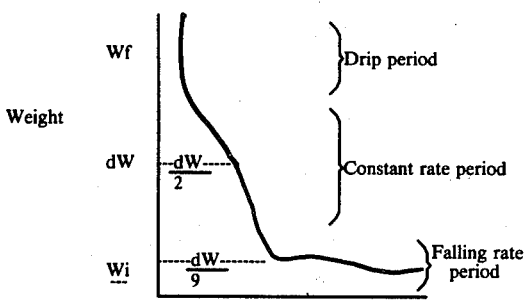

The drying of a wet solid follows the curve shown above. Initially, when the solid is removed from water, surface liquid rolls off giving rise to the steep slope of the drip period. The constant rate period, which follows the drip period, is a diffusion controlled process, whereby surface liquid saturates a stationary air "envelope" surrounding the hair. This moisture laden air is then carried into the main airstream.

When the drying surface can no longer saturate this envelope with water vapor, the falling rate period begins. Here the drying rate gradually falls off to zero, when the equilibrium moisture content or tare weight of the solid is reached.

Water uptake or pickup and drying time measurements are made by running a drying time curve. This involves the measurement of the weight of wetted hair over time as the hair dries. Water pickup is expressed as percent water pickup and is defined as the amount of moisture initially retained by the hair. It is calculated directly from the drying curve as follows:

$$\text{Percent water pickup} = \frac{Wf - Wi}{Wi} \cdot 100.0$$

Further, it has been determined that clean untreated hair will pick up on the average 124.4% of its weight in water. This allows us to define a relative water pickup value ($\alpha$) of a treated hair swatch as $$\alpha = \frac{\text{Percent water pickup}}{124.4\%}$$

Thus, the effect of hair treatments on water pickup can be easily assessed. It seems a fair assumption that drying time is directly proportional to amount of adsorbed water. We have therefore used water pickup and $\alpha$ values as measurements of fluoropolymer effectiveness.

Two time values from the drying curves have also been measured. They are $t_{.5}$ and $t_{.9}$ and are defined as the time required for the sample hair swatch to lose 0.5 and 0.9 of the adsorbed water respectively. The hair drying time ($t_{.5}$) gives a good indication of rapid water loss during the drip period, and establishes the slope of the constant rate period. Because of the decaying nature of the falling rate curve, the time required for the sample to come to total dryness (tare weight) is lengthy. Thus, $t_{.9}$ allows an economical estimate of "total" drying time without actually following the curve all the way to dryness.

A series of fluoropolymers in aqueous solution embraced in this invention were tested to determine their water repellency by the relative water uptake values ($\alpha$) and drying time ($t_{.9}$). A first run (Run 1) was made to serve as a control. In this case, hair swatches were first washed with an amphoteric or anionic surfactant solution defined more specifically below for 5 minutes. The hair was then rinsed thoroughly and combed. A drying curve was then run and the relative water pickup value ($\alpha$) and the drying time ($t_{.9}$) was determined for each surfactant treated. The weight of the hair at the end of the drip period is taken as the point in time that the water uptake is measured.

In Run 2, the hair was treated as for Run 1. In addition, after washing and rinsing the hair swatches were immersed in a 0.175% aqueous solution of the fluoropolymer for 5 minutes and then blow dried. The hair samples were then dipped in water for 5 minutes and a drying curve was run. As is the case with Run 1, the $\alpha$ value and the drying time ($t_{.9}$) values were determined.

Run 3 was a repeat of Run 2, and was intended to demonstrate the durability of the coating to water.

In the case of Run 4, this was also a repeat of Run 2, excepting that after the application of the fluoropolymer coating the hair samples were washed with a surfactant solution described in more detail below for 1 minute, rinsed, redipped into water after which the drying curve was run.

The results of these tests are summarized in Table I below. The composition of the amphoteric and anionic surfactant compositions used in these tests are as follows:

(1) Amphoteric

The solution used was a 1% (solids) aqueous solution of Miranol 2MCAS-Modified. The CTFA designation for this material is Amphoteric-6, and is described as a zwitterionic salt of a long chain imidazoline of the formula:

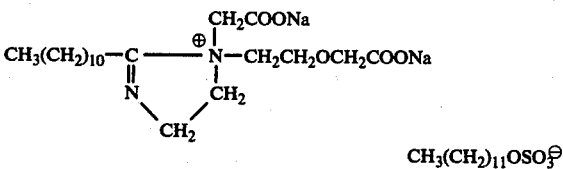

(2) Anionic

The treatment solution was made using 1% (solids) sodium lauryl ether (1 mole ethylene oxide) sulfate in water. The upper entry for each of the fluoropolymers in each of the Runs of Table I refers to the results obtained with hair swatches first washed with said amphoteric surfactant; whereas, the lower entry refers to the results obtained with hair swatches first washed with said anionic surfactant.

TABLE I

| DRYING CURVE RESULTS FOR FLUOROPOLYMERS | | | | | |
|---|---|---|---|---|---|
| Fluoropolymer | | Run 1 $\alpha/t_{.9*}$ | Run 2 $\alpha/t_{.9}$ | Run 3 $\alpha/t_{.9}$ | Run 4 $\alpha/t_{.9}$ |
| F 55 ± | (amphoteric) | 85.8/58 | 53.1/36 | 39.5/29 | 80.4/40 |
| F 55 − | (anionic) | 68.6/51 | 40.1/37 | 30.7/34 | 78.0/60 |
| F 56 ± | " | 73.0/58 | 50.0/34 | 35.4/27 | 75.5/54 |
| F 56 − | | 73.8/55 | 52.7/32 | 30.3/22 | 81.6/55 |
| F 57 ± | " | 103.7/65 | 43.3/26 | 34.9/22 | 97.2/62 |
| F 57 − | | 76.8/60 | 54.4/35 | 32.9/33 | 82.8/57 |
| F 58 ± | " | Insoluble | | | |
| F 58 − | | | | | |
| F 59 ± | " | 107.9/72 | 67.2/44 | 56.4/41 | 103.2/65 |
| F 59 − | | 129.9/64 | 67.0/40 | 32.2/23 | 100.5/65 |
| F 60 ± | " | 96.2/67 | 45.7/33 | 25.0/23 | 93.4/69 |
| F 60 − | | 92.9/67 | 37.9/41 | 28.7/28 | 88.4/66 |
| F 61 ± | " | 104.9/73 | 51.4/28 | — | 104.9/69 |
| F 61 − | | 117.2/62 | 42.2/25 | 35.6/21 | 93.6/53 |
| F 62 ± | " | 107.9/69 | 80.4/49 | 59.0/33 | 113.0/60 |

TABLE I-continued

| Fluoropolymer | | Run 1 α/t.9* | Run 2 α/t.9 | Run 3 α/t.9 | Run 4 α/t.9 |
|---|---|---|---|---|---|
| F 62 − | | 97.9/67 | 60.5/53 | 42.7/32 | 95.6/63 |
| F 63 ± | " | 82.3/62 | 38.2/32 | 33.3/38 | 87.2/66 |
| F 63 − | | 98.8/66 | 41.6/28 | 42.3/28 | 82.6/58 |
| F 64 ± | " | 124.5/78 | 43.1/35 | 37.2/33 | 110.6/77 |
| F 64 − | | 99.8/52 | 31.6/22 | 21.9/19 | 85.3/52 |
| F 65 ± | " | 109.3/59 | 46.6/31 | 33.0/32 | 117.3/63 |
| F 65 − | | 79.4/65 | 40.1/43 | 36.0/51 | 105.8/78 |
| F 66 ± | " | 132.7/76 | 64.5/51 | 64.5/54 | 104.7/84 |
| F 66 − | | 104.5/63 | 61.6/38 | 50.8/37 | 109.8/60 |
| F 67 ± | " | 126.5/74 | 87.0/48 | 59.3/38 | 135.7/69 |
| F 67 − | | 115.5/86 | 51.7/51 | 49.5/49 | 116.7/90 |

*α value given first. $t_{.9}$ follows the slash and is in minutes

A comparison of the results from Run 1 and Run 2 in each will show the increased water repellency following from the treatment of hair in accordance with the present invention. If we take, for example, the results obtained with fluoropolymer F-64, we find that in the case where hair is washed with the amphoteric surfactant, the relative pickup is 124.5% and that it takes 78 minutes for the hair to lose 90% of the water it adsorbed. In the corresponding case, where the hair was treated with the fluoropolymer solution in accordance with the present invention, the relative water pickup was reduced to 43.1% and the time for loss of 90% of the water adsorbed was reduced to 35 minutes.

Run 3 shows that these effects demonstrated in Run 2 survive two further rinsings of the hair. Run 4, on the other hand, demonstrates that the fluoropolymer coating applied to the hair in accordance with this invention is not resistant to shampoo treatment and may be removed when this is desired.

The following method was used to demonstrate that hair treated with the specified class of fluoropolymers in accordance with the present invention will retard the flow of sebum. The method used is described in U.S. Pat. No. 3,959,462. A solution of synthetic sebum having the composition given below was prepared by adding to a 600 ml beaker 0.40 gms. of sodium lauryl ether sulfate, 379.60 gms. of boiling water and 20.00 gms. of sebum. The entire mixture was slowly stirred with heating until the sebum was completely emulsified. The solution was cooled to 38° C. and used for testing the flow of sebum along swatches of treated and untreated hair. The composition of the synthetic sebum is as follows:

| Component | Grams/100 Grams |
|---|---|
| Lauric acid | 1 |
| Myristic acid | 2 |
| Palmitic acid | 7 |
| Stearic acid | 5 |
| Oleic acid | 10 |
| Linoleic acid | 5 |
| Coconut oil | 15 |
| Olive oil | 20 |
| Squalene | 5 |
| Cholesterol | 5 |
| Paraffin | 10 |
| Spermaceti | 15 |

The sebum is prepared by mixing the above ingredients together, heating them to 70° C., and allowing them to cool to room temperature.

EXPERIMENTAL PROCEDURE

Piedmont hair was freshly shampooed with a 1% solution of a commercial shampoo, rinsed thoroughly, and allowed to dry at 45° C. and 15% R.H. for three hours. Four of the swatches weighing approximately 2 g. each, were treated with a 0.175% aqueous solution of fluoropolymer F-64 for one minute until the remaining swatches were treated with distilled water. The hair swatches were dried again at 45° C. and 15% R.H. Two swatches of each treatment were vertically positioned on a glass rod and under each was placed a 50 ml. beaker filled with a sebum emulsion. Approximately 1–1.5 cm of the bottom of the swatches were immersed in the 5% sebum solution for 45 minutes after which they were placed in a dessicator containing osmium tetroxide for one hour. The fluoropolymer treated swatches showed no sign of sebum migration while the untreated samples showed a rise of 2.9 and 3.0 cm. as indicated by staining of the hair above the line of submersion in the sebum solution.

As noted above, it is a feature of this invention that hair treated in accordance with the present process exhibits a reduction in its dry coefficient of friction when compared with untreated hair which results in an improved dry combability for the hair. This is important in that the treatment of the hair by this process does not add the negative of increasing the resistance of the hair to combing while it increases its water and oil repellency. If this were the case, the advantage of increased water and oil repellency would be offset by the disadvantage of increased resistance to dry combing.

To measure the coefficient of resistance of hair treated according to the present invention, three solutions were prepared identified by the codes 3774-31B, 3774-22A and 3774-32B. Hair swatches were treated by immersing the swatches in the respective solutions for 5 minutes. The peak combing load (P.C.L.) was then determined for each hair sample both in the wet state and the dry state. The procedure for making these measurements is described in "Combability Measurements on Human Hair" Mario L. Garcia and Jose Diaz, J. Soc. Cosmet. Chem., 27, 379–398 (September 1976).

The results of these tests are summarized in Table II below. A positive number in the Table indicates an increase in resistance to combing when compared with untreated hair; whereas, a negative number indicates a decrease in resistance to combing.

TABLE II

| | | % Change in P.C.L. | |
|---|---|---|---|
| | | Wet | Dry |
| 3774-31B | | | |
| Fluoropolymer F-65 | 0.175% | +3 | −74 |
| Amphoterge S | 0.0175% | | |
| Water q.s. | 100% | | |
| 3774-32A | | | |
| Amphoterge S | 0.0175% | +18 | −55 |
| Water q.s. | 100% | | |
| 3774-32B | | | |
| Fluoropolymer F-65 | 0.175% | +74 | −42 |
| Water q.s. | 100% | | |

Note:
The wet combing forces were obtained using .175 aqueous fluoropolymer solutions It will be noted from Table II that for the hair samples treated with fluoropolymer solutions 3774-31B or 3774-32B, there is a decrease in the resistance to dry combing when compared with untreated hair. A similar reduction is also noted when the surfactant Amphoterge S is used alone. However, the combination of the fluoropolymer and the surfactant gives a result which is better than either the fluoropolymer alone or the surfactant alone, indicating a synergistic effect.

When the surfactant is employed in the composition used to treat air in accordance with the present invention, the quantity of surfactant used can vary somewhat. Usually, however, it will constitute between about 0.01% to 1.0% by weight based on the weight of the treating composition.

What is claimed is:

1. A process for treating human hair to reduce its critical surface tension and its coefficient of friction which comprises treating said hair with an effective amount of a composition comprising a carrier selected from the group consisting of liquids, creams, gels, foams, and aerosol propellant systems and about 0.005% to about 30% by weight of a fluoropolymer comprising:

(a) from about 60% to about 90% by weight of units derived from a monomeric fluoroalkylmethacrylate of the formula:

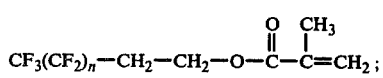

(b) from about 5% to 25% by weight of units derived from a monomeric aminoalkylmethacrylate of the formula:

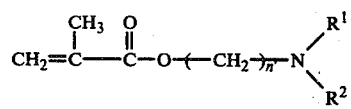

its N-oxides or its salts; and (c) from about 0 to 10% by weight of units derived from a monomeric ethylenedimethacrylate of the formula:

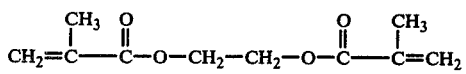

wherein:

(d) n is a number of about 7 to 11 inclusive;
(e) n' is a number of about 2 to 4 inclusive; and
(f) $R^1$ and $R^2$ are lower alkyl having 1 to 4 carbons
and wherein:
(g) the sum of percentages of said monomers contained in said fluoropolymers is 100%.

2. A process according to claim 1 in which said carrier is an aqueous carrier.

3. A process according to claim 1 in which said carrier is an aqueous solution.

4. A process according to claim 1 in which the fluoropolymer contains from about 0.01% to about 10% by weight of monomer c.

5. A process according to claim 1 in which said fluoropolymer is present in said composition in an amount in the range of from about 0.01% to about 10% by weight based on the total weight of the composition 6. A process according to claim 1 in which monomers (a), (b) and (c) are present in said fluoropolymer in the ratio of 84.98/15/0.02.

7. A process according to claim 1 in which said hair is dried after said treatment by blow drying it with drying means adapted to deliver a stream of hot air.

8. A process according to claim 1 in which said hair is towel or air dried after said treatment.

9. A process according to claim 1 in which said composition contains a surfactant.

10. A process according to claim 9 wherein said surfactant is an amphoteric surfactant.

11. A process according to claim 9 in which the surfactant is present in the range of from about 0.01% to about 1.0% by weight based on the total weight of the treating composition.

12. A process according to claim 1 wherein the monomeric fluoralkylmethacrylate is a mixture of the compounds of the formula:

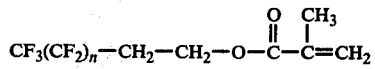

in which n is 7, 9 or 11 and wherein the monomeric aminoalkylmethacrylate is of the formula:

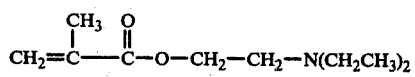

13. As a human hair treating composition of matter in combination an aqueous carrier, surfactant and about 0.005% to about 30% by weight of a fluoropolymer comprising:

(a) from about 60% to about 90% by weight of units derived from a monomeric fluoroalkylmethacrylate of the formula:

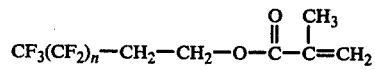

(b) from about 5% to 25% by weight of units derived from a monomeric aminoalkylmethacrylate of the formula:

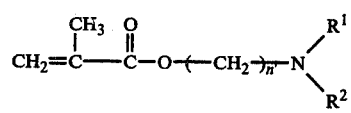

its N-oxides or its salts; and (c) from about 0 to 10% by weight of units derived from a monomeric ethylenedimethacrylate of the formula:

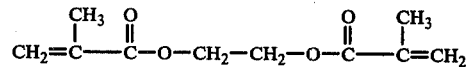

wherein:

(d) n is a number of about 7 to 11 inclusive;
(e) n' is a number of about 2 to 4 inclusive; and
(f) $R^1$ and $R^2$ are lower alkyl having 1 to 4 carbons
and wherein:
(g) the sum of percentages of said monomers contained in said fluoropolymer is 100%;
said fluoropolymer being present in sufficient amount to reduce the critical surface tension and coefficient of friction of hair treated with said composition.

14. A composition according to claim 13 wherein the surfactant is an amphoteric surfactant.

15. A composition according to claim 14 in which said surfactant is present in the range of from about 0.01% to about 1.0% by weight based on the total weight of said composition.

16. A composition according to claim 15 in which said polymer comprises from about 0.01% to 10% by weight of said composition.

17. A composition according to claim 13 in which the fluoropolymer contains from about 0.01% to about 10% by weight of monomer c.

18. A composition according to claim 13 wherein the monomeric fluoroalkylmethacrylate is a mixture of compounds of the formula:

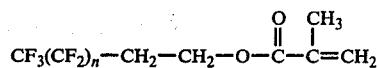

in which n is 7, 9 or 11 and wherein the monomeric aminoalkylmethacrylate is of the formula:

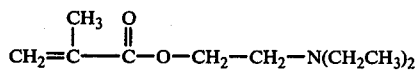

* * * * *

UNITED STATES PATENT AND TRADEMARK OFFICE
CERTIFICATE OF CORRECTION

PATENT NO. : 4,135,524

DATED : January 23, 1979

INVENTOR(S) : Ira E. Rosenberg et al

It is certified that error appears in the above-identified patent and that said Letters Patent are hereby corrected as shown below:

Column 10, Table I, line 65, change "96.2/67" to read -- 91.2/67

Column 13, line 2, change "air" to read -- hair --

Signed and Sealed this

Seventeenth Day of April 1979

[SEAL]

Attest:

RUTH C. MASON
Attesting Officer

DONALD W. BANNER
Commissioner of Patents and Trademarks